United States Patent [19]

Garvey et al.

[11] Patent Number: 5,011,690

[45] Date of Patent: Apr. 30, 1991

[54] SPHEROIDAL SILICA

[75] Inventors: Michael J. Garvey, Wirral; Ian C. Griffiths, Merseyside; John H. S. Rennie, Cheshire, all of England

[73] Assignee: Unilever Patent Holdings B.V., Rotterdam, Netherlands

[21] Appl. No.: 202,563

[22] Filed: Jun. 6, 1988

Related U.S. Application Data

[63] Continuation of Ser. No. 937,112, Dec. 2, 1986, Pat. No. 4,778,667.

[30] Foreign Application Priority Data

Jun. 5, 1987 [GB] United Kingdom ................ 8713263

[51] Int. Cl.$^5$ .......................... A61K 9/08; A61K 9/50; A61K 7/46; B32B 5/16
[52] U.S. Cl. ...................................... 424/401; 424/78; 424/79; 424/81; 424/408; 424/409; 424/499; 424/501; 426/650; 428/402.24; 512/4
[58] Field of Search .................... 424/401, 78, 79, 81, 424/408, 409, 499, 501; 428/402.24; 512/4; 426/650

[56] References Cited

U.S. PATENT DOCUMENTS

| | | | |
|---|---|---|---|
| 3,939,260 | 2/1976 | Lafon | 424/401 |
| 4,183,911 | 1/1980 | Smithies et al. | 424/401 |
| 4,255,286 | 3/1981 | Berek et al. | 423/338 |
| 4,708,859 | 11/1987 | Chevallier | 423/335 X |
| 4,752,459 | 6/1988 | Pepper | 423/339 X |
| 4,762,736 | 8/1988 | Garvey et al. | 427/214 X |
| 4,772,511 | 9/1988 | Wood et al. | 428/331 X |
| 4,778,667 | 10/1988 | Garvey et al. | 423/335 |

FOREIGN PATENT DOCUMENTS

| | | |
|---|---|---|
| 86309410 | 1/1987 | European Pat. Off. . |
| 1529058 | 6/1968 | France ............................. 423/339 |
| 74253 | 7/1970 | German Democratic Rep. ............................. 423/339 |
| 1433242 | 10/1974 | United Kingdom . |
| 2127002 | 8/1976 | United Kingdom . |
| 1506114 | 4/1979 | United Kingdom . |
| 1452896 | 3/1981 | United Kingdom . |

Primary Examiner—Thurman K. Page
Attorney, Agent, or Firm—Cushman, Darby & Cushman

[57] ABSTRACT

Porous spheroidal silica having a particle size in the range 1 to 400 microns, axial ratios of 1:1 to 1:12 has up to 50% by weight of the SiO$_2$ of included material, such as for example perfumes, flavoring materials, pigments, germicides, bactericides, fungicides, bleaching agents, skin benefit agents, therapeutic agents, dispe. ;ed in the silica as particles or droplets in the size range 0.01 to 10 μm. The spheroids can be made by mixing together an aqueous, stabilized silica sol containing dispersed therein up to 50% by weight of the silica of an included material and an aqueous solution of a non-adsorbing polymer to form a phase separated system comprising silica droplets containing included material in a polymer-rich continuous phase and condensing the silica sol to aggregate the droplets to form silica spheroids containing the dispersed included material. The included material can be released in use by e.g. wetting, attrition, dissolution, pH change, heating.

13 Claims, No Drawings

SPHEROIDAL SILICA

This application is a continuation of Ser. No. 06/937,112, filed Dec. 2, 1986 and now U.S. Pat. No. 4,778,667.

This invention relates to the formation of spheroidal silica aggregates. More particularly the invention relates to novel spheroidal silica aggregates comprising included materials and a process for the production of such silica aggregates.

In European Patent Application No 86309410.8 novel spheroidal silica aggregates are disclosed, which are generally rounded particles in the micron size range, for example in the range 1 to 400 microns.

In this above-mentioned European patent application there is disclosed and claimed a process for the preparation of novel silica spheroids comprising mixing together under alkaline conditions an aqueous alkali stabilised silica sol and an aqueous solution of a non-adsorbing polymer to form a phase separated system comprising silica droplets in a polymer rich continuous aqueous phase and acidifying the system to aggregate the droplets to form the silica spheroids.

It has now been found that certain other materials can be entrapped within the silica spheroids to form silica spheroids comprising included materials.

The included materials can be liquid or solid, organic or inorganic, or any mixture of these materials, but they must not induce visible aggregation of the silica sol.

This invention provides a porous spheroidal silica having a particle size in the range 1 to 400 microns, axial ratios of 1:1 to 1:12, and up to 50% by weight of the $SiO_2$ of included material dispersed in the silica as particles or droplets in the size range 0.01 to 10 $\mu$m.

This invention also provides a process for the preparation of the silica spheroids containing included materials comprising mixing together, an aqueous, stabilised silica sol containing, dispersed therein, up to 50% by weight of the silica of an included material and an aqueous solution of a non-adsorbing polymer to form a phase separated system comprising silica droplets containing included material in a polymer-rich continuous phase and condensing the silica sol to aggregate the droplets to form the silica spheroids containing the dispersed included material.

The porous spheroidal silica preferably has a pore volume in the range 26 to 50% and a narrow pore size distribution in which more than 80% of the porosity is between 50 and 200% of the median pore diameter in the pore size range 20 to 1000 Å. The references to pore volume and pore size of the spheroidal silica throughout the present specification relate to the dimensions of the porous silica in the absence of any included material.

The present invention can thus provide a means for carrying a material. Suitably the silica spheroids having the included material can be incorporated as a component in a composition. The silica spheroids are generally greater than one micron in diameter.

Examples of suitable included materials include perfumes, flavouring materials, pigments, germicides, bactericides, fungicides, bleaching agents, skin benefit agents, other therapeutic agents and mixtures thereof. Examples of compositions having the present silica materials as components include anti-perspirant and deodorant type products and cleaning compositions.

Suitably the included material comprises from 0.02 to 50% by weight of the silica more preferably 0.1 to 20% by weight of the silica. The actual amount will depend on the included material and the use to which it is intended to be put. Release of the material in use can be by any of a number of appropriate means e.g. wetting, attrition, dissolution, pH change, heating.

Preferably the present process includes admixing the material to be included with the silica sol prior to contact with the non-adsorbing polymer, suitably in the form of an emulsion in the presence of a surfactant.

Silica sols useful in this invention are typified by Ludox HS 40 (E I Du Pont de Nemours & Co) and the preparation of such sols is described in, for example, US Patent Specification 2 801 902. Such sols can have a concentration between ½% up to 55% by weight silica. In general, sol particle sizes of up to about 1000 Å may be used.

A preferred polymer concentration to induce phase separation is in the region 0.1 to 20% by weight in the mixture, more preferably in the region 2 to 20% by weight. The concentration of polymer is in addition related to the concentration of silica and the included material and the ionic type and concentration of electrolytes in the system. For example some electrolytes may be present in the original silica sol to control its stability and/or colloid stabilisers such as surfactants may be present in order to control the stability of a dispersion of the material to be included in the silica.

The most preferred concentration cannot be expressed simply, since this is a complex function of the polymer type, charge and flexibility, the electrolyte type and concentration, the silica sol type and concentration and the included material. Generally however the weight ratio of silica sol to polymer in the mixed phase system will lie within the range 1:10 to 100:1, more specifically within the range 1:1 to 50:1.

In carrying out the present process the silica sol can be stabilised under alkaline or acidic conditions. In practice the silica sol is more stable under alkaline conditions and this option is preferred. The possibility of performing the process using an acid stabilised silica sol can however be of value where the included material is itself more stable under acid than alkaline conditions. Condensation of the silica sol, by which we mean the irreversible fusing together of separate particles of the silica sol to form discrete beads of material, occurs readily between pH 4 and 8 and is fastest at a pH of around 6. Condensation is negligable above about pH 8, but does however occur slowly over a period of time below about pH 4. Condensation of the silica sol can thus occur by acidifying an alkali stabilised silica sol, by raising the pH of an acid stabilised silica sol or by maintaining an acid stabilised silica sol under acidic conditions for a sufficient period of time for example at least 48 hours, optimally 72 hours.

Thus in one embodiment of the present process the silica sol is alkali stabilised, the silica sol containing dispersed therein the included material and the said polymer are mixed together under alkaline conditions and the silica sol is condensed by acidification. Suitably the sol and polymer solutions are mixed together at a pH in the range 8.0 to 10.5 and the silica sol is acidified by reducing the pH to between 4 and 8 in a stepwise manner. In another embodiment of the present process the silica sol is acid stabilised, the silica sol containing dispersed therein the included material and the said polymer are mixed together under acid conditions and the silica sol is condensed by raising the pH of the sol. Suitably the silica sol and polymer solutions are mixed together at a pH between 0 and 4.0 and the silica sol is condensed by raising the pH to between 4 and 8. In yet another embodiment the silica sol is acid stabilised, the silica sol containing dispersed therein the included material and the said polymer are mixed together at a pH between 0 and 4.0 and the silica sol is condensed by maintaining the silica sol pH between 0 and 4.0.

The preferred embodiment comprises use of alkali stabilised silica sol and mixing the silica sol and polymer solutions together at a pH in the range 8.0 to 10.5. The process of aggregation or gelation of the silica droplets and the material to be included is initiated by the addition to the system of a mineral acid such as sulphuric or hydrochloric acid, although other acids may alternatively be used. The amount of acid required to induce the gelation or aggregation is that required to reduce the pH of the mixture to below that of the stable silica sol generally to within the range pH 4 to 8, preferably in the range pH 5 to 8. A further reduction in pH may be desirable to enhance the recovery of the spheroids from the polymer solution to as low as pH 2. The various pH reductions required in the process affect the final state of the silica spheroids and, as will be seen in the examples, significant time spans are involved and stepwise additions of acid are preferred.

Non-adsorbing polymers useful in the process are typically organic polymers. It is essential if phase separation is to be achieved that the polymer is not adsorbed by silica at the pH of the system. Examples of polymers suitable for use with alkali stabilised silica sol include negatively charged polyelectrolytes including, for example, sodium dextran sulphate, sodium polyacrylate, sodium carboxymethyl cellulose and mixtures of such polyelectrolytes. Examples of polymers suitable for use with acid stabilised silica sol include dextran, polyacrylic acid and mixtures thereof.

The most preferred concentration, of polymer can be obtained by the following procedure which, in addition, serves as a test procedure for selecting suitable polymers for the process.

A polymer type and concentration is selected by preparing an aqueous polymer solution in the region of up to 20% w/w and adding this slowly to a mixed dispersion of a silica sol and the material to be included in the concentration region of 20% w/w at an approximate pH 9 or pH 3 as appropriate, until the mixture just becomes appreciably more turbid. The mixture is allowed to mix thoroughly. If the turbidity decreases appreciably, more polymer is added until the mixture remains turbid after thorough mixing. The polymer concentration in the mixture would be in the region of 0.1 to 10% w/w and typically in the region 1 to 5% w/w based on the mixture. The phase separation state is confirmed by addition of an equal volume of water to the mixture which results in a dramatic decrease in turbidity, back to that of the order of the original silica sol and the included material.

Higher polymer concentrations can be used, as long as reversibility is observed on dilution to below the above-determined concentration of polymer. Unsuitable polymer types, levels or molecular weights will not result in the above reversible phase separation.

Undesirable irreversible turbidity would be due to aggregation rather than phase separation and may be caused by:

(i) excessive polyelectrolyte or electrolyte;
(ii) adsorbing rather than non-adsorbing polymers, e.g. cationic polyelectrolytes.

The above process of phase separation is discussed in "Polymeric Stabilisation of Colloidal Dispersions" by Donald H Napper, Academic Press 1983, and is understood to occur by a depletion flocculation mechanism. Phase separation is, therefore, more readily achieved with polymers of high molecular weight and high anionic charge density.

Certain anionic polymers such as xanthan gum, of very high molecular weight, will induce phase separation but because of their gelling characteristics are difficult to handle and are, therefore, less desirable than, for example, sodium dextran sulphate.

The silica spheroids prepared according to the present invention generally have the size in the range 1 to 400 microns, preferably in the range 1 to 200 microns. Sub-micron aggregates may be present as unwanted material at the end of the process.

Embodiments of the present invention will now be described by way of example only with reference to the following Examples.

EXAMPLE 1

10.2 g of an emulsion, prepared by dispersing, using ultrasonics, 0.5 g of perfume (Givaudan SN 15557) in 15.3 g of $10^{-2}$M sodium dodecyl sulphate, was thoroughly mixed with 55.3 g of a 30% w/w $SiO_2$ dispersion (Ludox HS40). This dispersion was added, with stirring, to 69.1 g of a 4% w/w polyacrylic acid solution the pH of which had been adjusted to pH 9.6, and maintained dispersed by stirring.

After one hour the pH of the system was reduced from 9.7 to 7.8 and then to 7.0 after a further hour. After 24 hours stirring was stopped and the dispersion was adjusted to pH2 and allowed to settle for 24 hours. The sediment was recovered and washed (four times) by redispersing in distilled water and leaving to settle for 24 hours.

Microscopic examination of the material showed it to consist of spheroidal silica particles of size up to 75 $\mu$m containing spherical droplets approximately 2 $\mu$m in diameter. A sample of silica spheroid slurry was allowed to dry at 60° C. to a powder which had a low perfume odour. On rewetting with water an appreciable increase in perfume odour was observed.

EXAMPLE 2

9.5 g of a 1% w/w ultramarine blue dispersion (micronised) and 48.4 g of Ludox HS40 (41.2% w/w $SiO_2$) were thoroughly mixed and added, with stirring, to 57 g of a 4% w/w polyacrylic acid solution the pH of which had been adjusted to pH 9.6. The sample was maintained dispersed by stirring.

After 2 hours the pH of the system was reduced from 9.7 to 7.8 and then to 7.0 after a further 2 hours. After a further 24 hours stirring was stopped and the sample allowed to settle.

Microscopic examination of the sediment showed it to consist of spheroidal silica particles containing pigment particles within them.

EXAMPLE 3

36 g of Ludox HS40 (41.2% w/w $SiO_2$) and 14 g of a cadmium alumino silicate pigment (Green DC 1543) were thoroughly mixed and added, with stirring, to 50 g of a polyacrylic acid solution the pH of which had been adjusted to pH 9.6. The sample was maintained dispersed by stirring.

After 2 hours the pH of the system was reduced from 9.7 to 7.8, and then to 7.2 after 2 hours and finally to 7.0 after a further hour. After 24 hours stirring was stopped and the sample allowed to settle.

Microscopic examination of the sediment showed it to consist of spheroidal silica particles with pigment particles contained within them.

EXAMPLE 4

12.5 g of an emulsion, prepared by dispersing, using ultrasonics, 2.5 g of perfume (Givaudan SN 15557) in 10 g of a dispersion containing 5% w/w $SiO_2$ (Ludox HS40) and 0.015% w/w cetyl trimethyl ammonium bromide, was dispersed into 37.5 g Ludox HS40 (41.2% w/w $SiO_2$). This dispersion was added, with stirring, to 50 g of a 4% w/w polyacrylic acid solution the pH of which had been adjusted to 9.6. The sample was maintained dispersed by stirring.

After 2 hours the pH of the system was reduced from 9.7 to 7.8 and then to 7.0 after a further 2 hours and finally to 2.3 after a further 72 hours. After 5 hours at pH 2.3 stirring was stopped and the sample allowed to settle.

Microscopic examination of the sediment showed it to consist of spheroidal silica particles containing spherical droplets 2 to 5 μm in diameter within them. A sample of the silica spheroid slurry was allowed to dry at 60° C. to give a powder with a low perfume odour which was markedly increased on rewetting with water.

EXAMPLE 5

An emulsion was prepared by dispersing 0.5 g of perfume (Vera 2 ex Firmenich) in 15.3 g of sodium dodecyl sulphate ($10^{-2}$M) using a sonic probe for 2 minutes. 10.2 g of this emulsion was then thoroughly mixed with 55 g of a 30% w/w dispersion of silica (Ludox HS40). The resulting mixture was then added with stirring to a 4% w/w solution of polyacrylic acid (BDH, molecular weight 230,000), the pH of which had been adjusted to 9.6 with concentrated sodium hydroxide solution. This final mixture was stirred on a magnetic stirrer for about 3 hours at room temperature and the pH was then adjusted to 8.1 using concentrated hydrochloric acid and the mixture stirred overnight. The pH was then reduced further to pH 7.0 and the mixture stirred gently for a further 24 hours.

The magnetic stirrer bar was removed and the mixture allowed to sediment. Supernatant liquid was discarded and replaced by an approximately equal volume of distilled water. The mixture was redispersed and allowed to sediment overnight. This process was repeated twice more.

Examination of the resulting sample under a microscope showed particles having a diameter of about 10 microns.

EXAMPLE 6

The procedure of Example 5 was repeated with the difference that the mixture was only stirred very gently following admixture of the perfume/sodium dodecyl sulphate/silica mixture with the polyacrylic acid solution and each of the two subsequent acidification steps. The relevant pH values at each step were 9.7, 8.0 and 7.0 respectively.

As in Example 5 the supernatant liquid was discarded and the product washed three times. The resulting particles had a size within the range of from about 10 to about 100 microns.

EXAMPLE 7

The procedure of Example 6 was followed with the exception that the sodium dodecyl sulphate was employed at a lower concentration equivalent to $10^{-3}$M. The relevant pH values were 9.7, 8.0 and 7.0 respectively. The resulting particles had a diameter within the range of from about 10 to about 100 microns.

EXAMPLE 8

The general procedure of Example 5 was followed. 10.2 g of an emulsion, prepared by dispersing 2.5 g of perfume (Vera 2 ex Firmenich) in 15.0 g of $10^{-2}$ m sodium dodecyl sulphate using a sonic probe, was thoroughly mixed with 55.3 g of a 30% w/w dispersion of silica (Ludox HS40). The resulting dispersion was added, with stirring, to 69.1 g of a 4% w/w polyacrylic acid solution at pH 9.6 and was maintained in a dispersed state by stirring. After 2 hours the pH was reduced from 9.8 to 8.9 and after a further 2 hours to 8.1.

After a further 24 hours with continued stirring the pH was reduced to 7.0 and stirring continued for a further 24 hours. The stirring was then stopped and the dispersion allowed to settle for 24 hours. The resulting sediment was recovered and washed four times by redispersing in distilled water and leaving to settle for 24 hours. The pH was reduced to 2.8. The final mixture was then filtered and left in the open air to dry thoroughly.

The resulting product was spheroidal particles of silica containing droplets of perfume.

EXAMPLE 9

An emulsion was prepared by dispersing using an ultrasonic probe 2.5 g of a perfume (Vera 2 ex Firmenich) in 10 g of a dispersion containing 5% w/w silica (Ludox HS40) and 0.015% w/w cetyl trimethyl ammonium bromide. This emulsion was then dispersed into 37.5 g of a 41.2% w/w dispersion of silica (Ludox HS40) and the mixture added with stirring to 50 g of a 4% w/w polyacrylic acid solution, the pH of which had been previously adjusted to 9.6 with a concentrated sodium hydroxide solution.

The resulting mixture had a pH of 9.7 and was stirred gently on a magnetic stirrer for 4 hours. The pH was then reduced to 8.0 by the addition of concentrated hydrochloric acid and the stirring continued overnight. The pH was further reduced to 7.0 and stirring continued for 24 hours. The pH was then reduced to 2.3 and the mixture stirred overnight. At this stage particles of diameter within the range of from about 10 to about 100 microns were observed under a microscope.

As in Example 5 the supernatant liquid was discarded and the product washed twice.

EXAMPLE 10

The general procedure of Example 9 was followed. An emulsion was prepared by dispersing 3.5 g Vera 2 ex Firmenich perfume in 9 g of a dispersion containing 5% w/w silica (Ludox HS40) and 0.015% w/w cetyl trimethyl ammonium bromide using an ultrasonic probe. The resulting emulsion was dispersed into 37.5 g of a 41.2% w/w dispersion of silica (Ludox HS40) and the mixture added with stirring to 50 g of a 4% w/w polyacrylic acid solution, the pH of which had been previously adjusted to 9.9 with concentrated sodium hydroxide solution. The mixture was then stirred gently on a magnetic stirrer for an hour. The pH was then reduced to 8.8 by the addition of concentrated hydrochloric acid and to 8.0 2 hours later. Stirring was continued overnight. The pH was then reduced to 7.0 and stirring continued for a further 24 hours. The stirring was then stopped and the mixture was diluted with 100 ml of distilled water. The pH was then reduced to 2.5 and the mixture was left to settle for 2 hours. The aqueous phase was then decanted off and the mixture redispersed. After an additional 2 hours the water was decanted off again and the mixture redispersed. The same washing procedure was repeated after a further 3 hours. The resulting mixture was filtered and left to air dry.

The resulting product consisted of spheroidal silica containing droplets of perfume.

EXAMPLE 11

The procedure of Example 5 was followed with the exception that a 2.4% w/w solution of sodium carboxymethylcellulose was employed in place of the polyacrylate solution. The complete mixture was initially stirred for 2 hours and its pH then reduced to 7.8. Stirring was continued for a further 2 hours, its pH then reduced to 7.0 and stirring continued overnight.

The product was washed as in Example 5. Ellipsoid or irregular aggregates having a size with the range of from about 10 to about 100 microns could be seen under a microscope.

EXAMPLE 12

The procedure of Example 11 was followed with the exception that Ludox SM silica was employed in place of Ludox HS40.

The product comprised spherical aggregates having a diameter of within the range of from about 10 to about 100 microns.

EXAMPLE 13

The procedure of Example 6 was followed with the exception that Vera 2 perfume was employed in an amount of 1.0 g instead of 0.5 g.

The resulting particles had a size within the range of from about 10 to about 100 microns.

EXAMPLE 14

The procedure of Example 13 was followed with the additional step of reducing the final pH of the mixture to 2.3 prior to washing.

The resulting particles had a size within the range of from about 10 to about 100 microns.

EXAMPLE 15

The procedure of Example 6 was followed with the exception that volatile silicone was employed as the emulsified oil in place of the perfume.

EXAMPLE 16

A comparative example was performed which followed the procedure of Example 14 with the exception that the emulsified perfume was added after the pH had been reduced to 2.3, i.e. after the silica spheroids had formed.

EXAMPLE 17

A comparative example was performed which followed the procedure of Example 6 with the exception that the emulsified perfume was added after the pH had been reduced to 7.0, i.e. after the silica spheroids had formed.

The products of Examples 6, 7, 9, 13, 14, 16 and 17 were analysed in order to assess the amount of perfume included in the silica particles. The results are given in Table I below.

TABLE I

| Example | Amount of perfume (w/w % w.r.t. silica) |
| --- | --- |
| 6 | 0.26 |
| 7 | 0.44 |
| 9 | 6 |
| 13 | 0.29 |
| 14 | 0.92 |
| 16 | 0.01 |
| 17 | 0.0 |

As can be seen from Table I those products in which the perfume was incorporated within the silica spheroids during aggregation of the silica to form the spheroids had significantly higher levels of included perfume than the comparative examples 16 and 17 in which the perfume was admixed with the ready formed silica spheroids.

The products of Examples 6, 13, 14 and 16 were assessed subjectively on a score rating for their perfume levels. Each product was assessed both in the dry state and after having been admixed with water. The testers did not know on testing whether the product was in a dry or wet state. The results are given in Table II below.

TABLE II

| Example | Dry | Wet |
| --- | --- | --- |
| 6 | 6 ± 10 | 50 ± 28 |
| 13 | 4 ± 6 | 66 ± 29 |
| 14 | 4 ± 6 | 58 ± 17 |
| 16 | 4 ± 6 | 29 ± 21 |

The score used increased with an increased detection of perfume. The results of Table II thus show that perfume was released from the products embodying the present invention (Examples 6, 13, 14) on wetting. There is a significant difference between the scores of the products on wetting between Examples 6, 13 and 14 and the comparative Example 16.

EXAMPLE 18

A suspension of diperoxydodecanoic acid (DPDA) in silica sol was prepared by reducing the pH of 33 g Ludox HS-40 silica sol to 3.0 and adding 17 g 40% DPDA aqueous slurry with stirring. This suspension was added with gentle stirring to 150 g of a 13.3% w/w solution of $2 \times 10^6$ molecular weight dextran, the pH of which had been previously adjusted to 3.0, and maintained dispersed by stirring for one hour. After an hour stirring was stopped, and the mixture was allowed to stand without stirring for 72 hours. The sediment was recovered and washed four times in 0.1M hydrochloric acid by dispersing and settling. Microscopic examination of the material showed it to consist of spheroidal silica particles up to 100 μm in size containing DPDA crystals having an average diameter within the range 1 to 5 μm.

EXAMPLE 19

A suspension of diperoxydodecanoic acid (DPDA) in silica sol was prepared by reducing the pH of 33g Ludox HS-40 silica sol to 3.0 and adding 17 g 40% DPDA aqueous slurry with stirring. This suspension was added with gentle stirring to 150 g of a 15% w/w solution of $2.3 \times 10^5$ molecular weight polyacrylic acid, the pH of which had been previously adjusted to 3.0, and maintained dispersed by stirring for one hour. After an hour stirring was stopped, and the mixture was allowed to stand without stirring for 72 hours. The sediment was recovered and washed four times in 0.1M hydrochloric acid by dispersing and settling. Microscopic examination of the material showed it to consist of spheroidal silica particles up to 100 $\mu$m in size containing DPDA crystals having an average diameter within the range 1 to 5 $\mu$m.

EXAMPLE 20

An emulsion of perfume (Givaudan SN 15557) was prepared by dispersing, using ultrasonics, 10 g perfume in a mixture of 33 g Ludox HS-40 silica sol, 2 g precipitated silica and 5 g 10% w/w sodium dodecyl sulphate solution, the pH of which had previously been adjusted to 3.0. This emulsion was added with gentle stirring to 150 g 15% w/w of $2.3 \times 10^5$ molecular weight polyacrylic acid solution, the pH of which had also been adjusted to 3.0. After stirring for half an hour, stirring was stopped and the mixture allowed to stand for 72 hours. The sediment was recovered and washed four times by resuspending in distilled water and settling. Microscopic examination of the material showed it to consist of spheroidal silica particles up to 100 $\mu$m in size containing perfume droplets having a diameter in the range 1 to 5 $\mu$m.

EXAMPLE 21

An emulsion of perfume (Givaudan SN 15557) was prepared by dispersing, using ultrasonics, 10 g perfume in a mixture of 33 g Ludox HS-40 silica sol, 2 g precipitated silica and 5 g 10% w/w sodium dodecyl sulphate solution, the pH of which had previously been adjusted to 3.0. This emulsion was added with gentle stirring to 150 g 13.3% w/w of $2 \times 10^6$ molecular weight dextran solution, the pH of which had also been adjusted to 3.0. After stirring for half an hour, stirring was stopped and the mixture allowed to stand for 72 hours. The sediment was recovered and washed four times by resuspending in distilled water and settling. Microscopic examination of the material showed it to consist of spheroidal silica particles up to 100 $\mu$m in size containing perfume droplets having a diameter in the range 1 to 5 $\mu$m.

We claim:

1. Process for the preparation of porous silica spheroids having a particle size in the range 1 to 400 microns and axial ratios of 1:1 to 1:12 and containing included material selected from the group consisting of perfumes, flavouring materials, pigments, germicides, bactericides, fungicides, bleaching agents, skin benefit agents, therapeutic agents and mixtures thereof, said process comprising the steps of
(i) mixing together (a) an aqueous, stabilized silica sol containing dispersed therein said included material in an amount of 0.02 to 50% by weight of the silica and (b) an aqueous solution of a polymer which is not adsorbed by the silica, so as to form a phase separated system comprising silica droplets containing said included material in a polymer-rich continuous phase, and
(ii) condensing the silica sol to aggregate the droplets to form said porous silica spheroids containing the included material.

2. A process according to claim 1 wherein in the case where the silica sol is alkali stabilized the non-adsorbing polymer is selected from the group consisting of sodium dextran sulphate, sodium polyacrylate, sodium carboxymethyl cellulose and mixtures thereof, and in the case where the silica sol is acid stabilized the non-absorbing polymer is selected from the group consisting of dextran, polyacrylic acid and mixtures thereof.

3. A process according to claim 1 including incorporating the porous spheroidal silica having the included material as a component in a composition.

4. Process according to claim 1 wherein the silica sol is alkali stabilised, the said polymer and the silica sol containing dispersed therein the included material are mixed together under alkaline conditions and the silica sol is condensed by acidification.

5. Process according to claim 4 wherein the sol and polymer solutions are mixed together at a pH in the range 8.0 to 10.5.

6. A process according to claim 4 wherein the silica sol is acidified by reducing the pH to between 4 and 8 in a stepwise manner.

7. A process according to claim 4 wherein the non-adsorbing polymer is selected from the group comprising sodium dextran sulphate, sodium polyacrylate, sodium carboxymethyl cellulose and mixtures thereof.

8. Process according to claim 1 wherein the silica sol is acid stabilised, the said polymer and the silica sol containing dispersed therein the included material are mixed together under acid conditions and the silica sol is condensed by raising the pH of the sol.

9. Process according to claim 8 wherein the silica sol and polymer solutions are mixed together at a pH between 0 and 4.0 and the silica sol is condensed by raising the pH to between 4.0 and 8.0.

10. Process according to claim 1 wherein the silica sol is acid stabilised, the said polymer and the silica sol containing dispersed therein the included material are mixed together at a pH between $-1.0$ and 4.0 and the silica sol is condensed by maintaining the silica sol ph between 0 and 4.0.

11. Process according to claim 8 wherein the non-adsorbing polymer is selected from the group comprising dextran, polyacrylic acid and mixtures thereof.

12. A process according to any one of claim 1 wherein the polymer concentration to induce phase separation is 0.1 to 20% by weight of the mixture.

13. A process according to claim 1 including admixing the included material with the silica sol prior to contact with the non-adsorbing polymer.

* * * * *